United States Patent [19]

Roman

[11] 4,409,398
[45] Oct. 11, 1983

[54] PREPARATION OF (1R, CIS)-OXYIMINO-SUBSTITUTED CYCLO-PROPANECARBOXYLIC ACIDS

[75] Inventor: Steven A. Roman, Fulshear, Tex.

[73] Assignee: Shell Oil Company, Houston, Tex.

[21] Appl. No.: 292,567

[22] Filed: Aug. 13, 1981

[51] Int. Cl.³ .......................................... C07C 131/02
[52] U.S. Cl. ............................... 562/506; 260/456 A; 260/464; 260/502.5 D; 260/503; 544/162; 546/235; 549/49; 549/68; 549/76; 549/305; 549/480; 549/496; 562/444; 562/500; 260/941
[58] Field of Search ............... 560/124; 562/500, 506, 562/444; 260/347.3, 456 A, 464, 502.5, 503, 941; 549/76, 305, 49, 68, 480, 491, 566; 544/162; 546/235

[56] References Cited

U.S. PATENT DOCUMENTS

| | | | |
|---|---|---|---|
| 3,723,469 | 3/1973 | Martel | 560/124 |
| 3,922,269 | 11/1975 | Elliott et al. | 260/347.4 |
| 4,132,717 | 1/1979 | Roman | 260/343.3 R |
| 4,211,789 | 7/1980 | Roman | 562/506 |
| 4,218,402 | 8/1980 | Roman | 562/506 |
| 4,235,780 | 11/1980 | Kondo | 260/343.3 R |
| 4,237,123 | 12/1980 | Roman | 424/200 |
| 4,257,956 | 3/1981 | Syrier | 260/343.21 |
| 4,282,249 | 8/1981 | Roman et al. | 424/304 |

OTHER PUBLICATIONS

Derwent Abstract of European Pat. 5,882.

*Primary Examiner*—Michael L. Shippen

[57] ABSTRACT

(1R,cis)-Oxyimino-substituted cyclopropanecarboxylic acids are prepared via a (1R,4R,5S)-4-acetoxy-6,6-dimethyl-2-oxo-3-oxabicyclo [3.1.0]hexane intermediate.

14 Claims, No Drawings

PREPARATION OF (1R, CIS)-OXYIMINO-SUBSTITUTED CYCLO-PROPANECARBOXYLIC ACIDS

BACKGROUND OF THE INVENTION

1. Field of the Invention

This invention relates to a process for the preparation of (1R,cis)-oxyimino-substituted cyclopropanecarboxylic acids.

2. Description of the Prior Art

U.S. Pat. Nos. 3,922,269 and 4,237,123 and European Pat. No. 5,882 each discloses pesticidal esters of oxyimino-substituted cyclopropanecarboxylic acids. The acids are prepared, for example, (1) by treating an alkyl ester of caronaldehydic acid with an equimolar amount of (an acid addition salt of) hydroxylamine or of a hydrocarbyloxyamine of the formula $R^1ONH_2$, wherein $R^1$ is hydrogen or certain optionally halogenated hydrocarbyl groups in a polar solvent; or (2) by treating a mixed anhydride of acetic and caronaldehydic acids with an acid addition salt of a hydroxylamine or a hydrocarbyloxyamine followed by hydrolysis of the oxyimino-substituted product as taught in U.S. Pat. No. 4,218,402.

SUMMARY OF THE INVENTION

The present invention is directed to the preparation of (1R,cis)-oxyimino-substituted cyclopropanecarboxylic acids via (1R,4R,5S)-4-acetoxy-6,6-dimethyl-3-oxabicyclo[3.1.0]hexan-2-one.

(1R,4R,5S)-4-acetoxy-6,6-dimethyl-3-oxabicyclo[3.1.0]-hexan-2-one itself is prepared either (1) by ozonolysis of (1R,cis)-4,7,7-trimethyl-3-oxabicyclo[4.1.0]hept-4-en-2-one followed by reduction of the ozonolysis product or (2) by treatment of (1R,cis)-caronaldehydic acid with acetic anhydride.

When this novel (1R,4R,5S)-4-acetoxy-6,6-dimethyl-3-oxabicyclo[3.1.0]-hexan-2-one isomer is prepared or subsequently used substantially free of all other possible isomers, it is desirably at least about 70% pure, although a purity above about 80% is preferable and a purity above about 95% is highly desirable.

The ozonolysis reaction is conducted with ozone, or preferably with a gaseous mixture comprising ozone and oxygen or ozone and air. The ozone or mixture of ozone and oxygen can be diluted with an inert gas, such as nitrogen or argon. The ozonolysis is carried out at atmospheric pressure at a temperature from about −80° C. to +20° C., preferably from about −60° to −80° C. A solvent is preferably used in the reaction. The solvent used can be any solvent which will not interfere with the reaction. Suitable solvents include aliphatic hydrocarbons, cycloaliphatic hydrocarbons, aromatic hydrocarbons, halogenated hydrocarbons, lower aliphatic carboxylic acids or lower alkyl esters thereof and lower alkanols or mixtures thereof. Alphatic and cycloaliphatic hydrocarbon solvents contain 5 to 10 carbon atoms, such as n-pentene, n-hexane, n-octane, n-heptane, n-nonane, n-decane and their isomers. Gasolines rich in alkanes are also suitable, for example, with a boiling range at atmospheric pressure of between about 40° to 65° C., of 60° to 80° C. or 80° to 110° C. Petroleum ether is also suitable. Aromatic hydrocarbon solvents contain from 6 to 10 carbon atoms, such as benzene, toluene, o-, m- and p- xylene, the trimethylbenzenes, p-ethyltoluene and the like. Suitable halogenated hydrocarbons contain 1 to 4 halogen atoms, preferably chlorine atoms, in combination with an alkane chain containing from 1 to 4 carbon atoms or with a benzene ring, such as carbon tetrachloride, trichloroethane, methylene chloride, chloroform, chlorobenzene and 1,2- and 1,3-dichlorobenzene. Acetic acid, ethyl acetate, methanol and ethanol are examples of the carboxylic acids, esters and alkanols. Ethyl acetate is preferred.

Reduction of the ozonolysis product may be carried out by various known agents. For example, the reduction may be carried out in the presence of hydrogen and a noble metal catalyst of Group VIII of the Periodic Table of Elements, supported on a carrier, such as palladium on carbon or other suitable reducing agents such as dimethyl sulfide. Palladium on carbon is a preferred catalyst for use with hydrogen to carry out the reduction, preferably in a Parr bomb or other pressure vessel. A reduction is carried out in the presence of a solvent or a source of acetate ions, which is preferably an alkali or alkaline earth metal acetate, potassium acetate or the like. Sodium acetate is preferred. Analogous reduction procedures are described in Harper, S. H. et al., *J. Sci. Food, Agr.,* 2 page 414 (1951), including use of palladium catalysts, and Pappas, James J., *Tetra. Letters,* 36, page 4273 (1966) on use of dialkyl sulfides.

In an alternative route, (1R,cis)-caronaldehydic acid is used as a starting material and is known from U.S. Pat. No. 3,723,269. In this alternative route, (1R,cis)-caronaldehydic acid is reacted with acetic anhydride suitably in the presence of an acid catalyst, such as acetic, hydrochloric and particularly sulfonic acids like p-toluenesulfonic acid. The reaction need not be conducted in the presence of a solvent, but, if desired, inert solvents, such as methylene chloride, a haloform, tetrahydrofuran or the like may be used. The reaction with acetic anhydride is conducted at temperatures conveniently in the range of from about −10° C. to about ambient temperatures or slightly above. Generally, the temperature is from about −5° to about 40° C., preferably from about −5° to 5° C. The molar ratio of the reactants in this step is not critical and can be varied widely. Generally, a molar ratio of the acid to the anhydride is from about 1.0 to about 1.6, and preferably from about 1.1 to about 1.4. The reaction between (1R,cis)-caronaldehydic acid and acetic anhydride is preferably conducted while agitating the reaction mixture, e.g. by stirring, and maintaining the desired reaction temperature. The resulting product may be purified or converted directly into the oxyimino-substituted cyclopropanecarboxylic acid as described below.

The final step of preparing the (1R,cis)-oxyimino-substituted cyclopropanecarboxylic acid comprises treating the (1R,4R,5S)-4-acetoxy-6,6-dimethyl-3-oxabicyclo[3.1.0]hexan-2-one with an acid addition salt of hydroxylamine or of an optionally substituted hydrocarbyloxy-amine in the presence of a base. The acid addition salt may be of any anion from a salt-forming acid, that will not interfere with the reaction. Suitable inorganic acids include hydrohalogenic acids, such as hydrochloric or hydrobromic, sulfur acids, such as sulfuric, and phosphorus acids, such as phosphoric acid, and organic acids, such as oxalic acid and the like, are also suitable to form the salts. This step is conducted in the presence of a solvent. Suitable solvents are those unreactive to hydroxylamines and which have some solubilizing properties for salts, e.g., chlorinated hydrocarbons, alcohols or esters. Suitable chlorinated hydrocarbons contain from 1 to 4 chlorine atoms in combination with an alkane chain containing from 1 to 4 carbon atoms or with a benzene ring, for example, carbon tetrachloride, chloroform, methylene chloride, 1,2- or 1,3-dichlorobenzene. Methylene chloride is a preferred chlorinated solvent. Alcohols are the preferred solvents and are alkanols containing from 1 to 6 carbon atoms, such as methanol, ethanol and the like. Suitable esters are those of lower alcohols and acids each containing from 2 to 6 carbon atoms, for example, ethyl acetate. The base may be an alkali or alkaline earth metal hydroxide or material capable of generating $OH^\ominus$ ions under the reaction conditions, for example, sodium hydroxide, potassium hydroxide and the like. The reaction temperature for the step is not critical and can range from about $-10°$ C. to about ambient temperatures or slightly above. Generally, the temperature is from about $-5°$ to $40°$ C., preferably from about $-5°$ to $5°$ C. The molar ratio of the reactants in the step is not critical and can be widely varied. Generally, a molar ratio of the acid addition salt to the oxabicyclohexane derivative is from about 1.0 to about 1.6, and preferably from about 1.1 to about 1.4. The step is usually conducted by adding the acid addition salt while agitating the reaction mixture, e.g., stirring, and maintaining the desired reaction temperature. The resulting 3-oxyimino-substituted product can be purified or used directly in the esterification to pesticidal esters.

The preparation of the (1R,cis)-oxyimino-substituted cyclopropanecarboxylic acids can be conducted in separate steps but is preferably conducted as a one pot reaction.

The present process is useful for the preparation of (1R,cis)-2,2-dimethyl-3-((oxyimino)methyl)cyclopropanecarboxylic acids of the formula

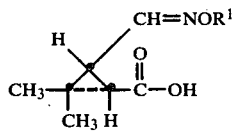

wherein $R^1$ represents a hydrogen atom, an alkyl group containing from 1 to 10 carbon atoms optionally substituted by one or more halogen atoms, a (cycloalkyl)alkyl group containing from 3 to 7 carbon atoms, a total of from 4 to 9 carbon atoms and optionally ring substituted by one or more halogen atoms, a cycloalkyl group containing from 3 to 7 ring carbon atoms, an alkenyl group containing from 2 to 4 carbon atoms optionally substituted by one or more halogen atoms or an alkynyl group containing from 2 to 4 carbon atoms or an aryl group containing from 6 to 12 carbon atoms or an aralkyl group containing from 7 to 10 carbon atoms, each optionally ring-substituted by one or more halogen atoms. The halogen atom substituents are chlorine, fluorine or bromine. These acids are especially useful to prepare pesticidal esters when $R^1$ is an alkyl group containing 3 to 6 carbon atoms or a (cycloalkyl)alkyl group containing 3 to 4 ring carbon atoms and a total of 4 to 5 carbon atoms, especially neopentyl, sec-butyl or cyclobutylmethyl.

$R^1$ may also be a group

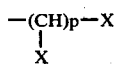

wherein X is thienyl, furfuryl, $-CO_2R^1$, $-CONR^1R^2$, $-SO_3R^1$, $-SO_2NR^1R^2$, $-PO(OR^1)_2$, $-NO_2$, $-CN$, $-OR^1$, $-SR^1$, $-S(O)R^1$, $-S(O)_2R^1$, $-NR^1R^2$, $-N(O)R^1R^2$ or $-(OCH_2CH_2)_q-OR^1$ in which $q$ is an integer of 1 to 4, $R^1$ and $R^2$ each independently is a hydrogen atom, an alkyl group containing from 1 to 8 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms or $R^1$ and $R^2$ taken together is an alkylene or oxaalkylene group containing from 4 to 6 carbon atoms, or when one $R^1$ or $R^2$ is furfuryl or thienyl then the other is a hydrogen atom; p is an integer of 1 or 2; when p is 1 then $X^1$ is an alkyl group containing from 1 to 4 carbon atoms or when p is 2 then $X^1$ is a hydrogen atom. These acids and pesticidal esters thereof are disclosed in U.S. Pat. No. 4,237,123.

The enol lactone starting material, (1R,cis)-4,7,7-trimethyl-3-oxabicyclo[4.1.0]hept-4-en-2-one, can be prepared by a process described in U.S. Pat. Nos. 4,132,717 and 4,156,692 from (+)-$\Delta^3$-carene, e.g., in which carene is subjected to ozonolysis, the resulting 2,2-dimethyl-3-(2-oxopropyl)cyclopropane-1-acetaldehyde is treated with acetic acid and triethylamine to give the corresponding enol acetate of the aldehyde. Ozonolysis of this intermediate followed by reduction with zinc dust in acetic acid gives (1R-cis)-2,2-dimethyl-3-(2-oxopropyl)cyclopropane-1-carboxaldehyde, which is oxidized with aqueous alkaline potassium permanganate or gaseous oxygen to afford the (1R,cis)-2,2-dimethyl-3-(2-oxopropyl)cyclopropane-1-carboxylic acid. This acid, as described in U.S. Pat. No. 4,132,717, is cyclodehydrated to the enol lactone, (1R,cis)-4,7,7-trimethyl-3-oxabicyclo[4.1.0]hept-4-en-2-one.

ILLUSTRATIVE EMBODIMENTS

The invention is illustrated by the following embodiments which describe the preparation of typical oxyimino-substituted cyclopropanecarboxylic acids by the invention. These embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

Embodiment I

A stream of ozone was bubbled into a solution of 7.2 g of (1R,cis)-4,7,7-trimethyl-3-oxabicyclo[4.1.0]hept-4-en-2-one in 50 ml of ethyl acetate at 0° C. for 1.5 hours at 1 l/min. until a blue color persisted. The solution was purged with nitrogen to remove excess ozone. The reaction mixture was added to 25.5 g of acetic anhydride, 50 ml of acetic acid and 4.1 g of sodium acetate and hydrogenated in a Parr bomb charged with 2.4 g of 10% palladium on charcoal. The resulting mixture was filtered and the filtrate was stripped of ethyl acetate and acetic acid. The resulting product was diluted with methylene chloride, washed with water, and the methylene chloride phase was dried (MgSO$_4$) and stripped to yield 5.7 g of the desired (1R,4R,5S)-4-acetoxy-6,6-dimethyl-3-oxabicyclo[3.1.0]hexan-2-one product as an oil.

Embodiment II

To a stirred solution of 2.0 g of (1R,cis)-caronaldehydic acid in 10 ml of acetic anhydride was added 0.05 g of p-toluenesulfonic acid. The resulting reaction was exothermic and the reaction mixture became light orange, the reaction subsiding after 15 minutes. The temperature was controlled at <30° C. with a water bath. The reaction mixture was stirred for about 1 hour at room temperature, then diluted with diethyl ether. The organic phase was washed with ice cold sodium bicarbonate solution, dried (MgSO₄) and stripped to yield a semi-solid, which upon recrystallization from 1:1 ether-pentane yielded 1.1 g of the desired (1R,4R,5S)-2-acetoxy-6,6-dimethyl-3-oxabicyclo[3.1.0]hexan-2-one product.

Embodiment III

A 184 mg sample of (1R,4R,5S)-4-acetoxy-6,6-dimethyl-3-oxabicyclo[3.1.0]hexane-2-one in 2.5 ml of 60% aqueous ethanol was treated with 835 mg of methoxyamine hydrochloride and 40 mg of sodium hydroxide at room temperature. After 4 hours, the resulting mixture was acidified to pH 2 with dilute hydrochloric acid, and extracted with methylene chloride. The organic phase was dried (MgSO₄) and stripped to yield 148 mg of the desired (1R,cis)-2,2-dimethyl-3-(methoxyimino)methyl)cyclopropanecarboxylic acid.

Embodiments IV–VII

Following procedures similar to Embodiments I, II and III above, (1R,cis)-2,2-dimethyl-3-((cyclobutylmethoxyimino)methyl) cyclopropanecarboxylic acid (Embodiment IV), (1R,cis)-2,2-dimethyl-3-((cyclopropylmethoxyimino)methyl)cyclopropanecarboxylic acid (Embodiment V), (1R,cis)-2,2-dimethyl-3-(neopentoxyimino)methyl)cyclopropanecarboxylic acid (Embodiment VI), (1R,cis)-2,2-dimethyl-3-((isobutoxyimino)methyl)cyclopropanecarboxylic acid (Embodiment VII) are obtained.

I claim:

1. A process for the preparation of (1R,4R,5S)-4-acetoxy-6,6-dimethyl-3-oxabicyclo[3.1.0]hexan-2-one which comprises treating (1R,cis)-4,7,7-trimethyl-3-oxabicyclo[4.1.0]hept-4-en-2-one with ozone and reducing the product formed by this ozonolysis in the presence of hydrogen and a noble metal catalyst of Group VIII.

2. A process according to claim 1 wherein the ozone is a mixture of ozone with oxygen, nitrogen, argon or air.

3. A process according to claim 2 wherein the treatment with ozone is conducted in the presence of a solvent.

4. A process according to claim 3 wherein the solvent is selected from an aliphatic hydrocarbon, a cycloaliphatic hydrocarbon, an aromatic hydrocarbon, a halogenated hydrocarbon, a lower aliphatic carboxylic acid or lower alkyl ester thereof or a lower alkanol or mixtures of such solvents.

5. A process according to claim 1 wherein the catalyst is palladium on carbon.

6. A process according to claim 1 wherein reduction is carried out in the presence of a source of acetate ions which is an alkali or alkaline earth metal acetate.

7. A process according to claim 6 wherein the acetate is sodium acetate.

8. A process for the preparation of a (1R,cis)-oxyimino-substituted cyclopropanecarboxylic acid of the formula

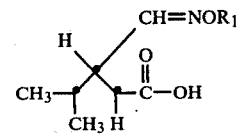

wherein R₁ represents a hydrogen atom; an alkyl group containing from 1 to 10 carbon atoms optionally substituted by one or more halogen atoms; a (cycloalkyl)alkyl group containing from 3 to 7 carbon atoms, a total of from 4 to 9 carbon atoms and optionally ring-substituted by one or more halogen atoms; a cycloalkyl group containing from 3 to 7 ring carbon atoms; an alkenyl group containing from 2 to 4 carbon atoms optionally substituted by one or more halogen atoms; an alkynyl group containing from 2 to 4 carbon atoms; an aryl group containing from 6 to 12 carbon atoms; an aralkyl group containing from 7 to 10 carbon atoms, each optionally ring-substituted by one or more halogen atoms; or a group

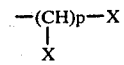

wherein X is thienyl, furfuryl, —CO₂R¹, —CONR¹R², —SO₃R¹, —SO₂NR¹R², —PO(OR¹)₂, —NO₂, —CN, —OR¹, —SR¹, —S(O)R¹, —S(O)₂R¹, —NR¹R², —N(O)R¹R² or —(OCH₂CH₂)q—OR¹ in which q is an integer of 1 to 4, R¹ and R² each independently is a hydrogen atom, an alkyl group containing from 1 to 8 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms, an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms, or R¹ and R² taken together is an alkylene or oxaalkylene group containing from 4 to 6 carbon atoms, or when one R¹ or R² is furfuryl or thienyl then the other is a hydrogen atom; p is an integer of 1 or 2; when p is 1 then X¹ is an alkyl group containing from 1 to 4 carbon atoms or when p is 2 then X¹ is a hydrogen atom, which process comprises treating (1R,cis)-4,7,7-trimethyl-3-oxabicyclo-[4.1.0]hept-4-en-2-one with ozone and then reducing the product formed by this ozonolysis in the presence of hydrogen and a noble metal catalyst of Group VIII, and treating the resulting (1R,4R,5S)-4-acetoxy-6,6-dimethyl-3-oxabicyclo[3.1.0]-hexan-2-one with an acid addition salt of the corresponding hydroxylamine or optionally substituted hydrocarbyloxyamine in the presence of a base.

9. A process according to claim 8 wherein the treatment is conducted in the presence of a solvent.

10. A process according to claim 9 wherein the solvent is an alcohol.

11. A process according to claim 10 wherein the alcohol is ethanol.

12. A process according to claim 8 wherein the acid addition salt is a hydrobromide or hydrochloride.

13. A process according to claim 8 wherein $R^1$ is an alkyl group containing 3 to 6 carbon atoms or a (cycloalkyl)alkyl group containing 3 to 4 ring carbon atoms and a total of 4 to 5 carbon atoms.

14. A process according to claim 13 wherein $R^1$ is neopentyl, sec-butyl or cyclobutylmethyl.

* * * * *